(12) United States Patent
Ludwig

(10) Patent No.: US 11,559,235 B2
(45) Date of Patent: Jan. 24, 2023

(54) PACING DEVICE WITH AUTONOMOUS ANTI-TACHYCARDIA PACING

(71) Applicant: Cardiac Pacemakers, Inc., St. Paul, MN (US)

(72) Inventor: Jacob M. Ludwig, Isanti, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 630 days.

(21) Appl. No.: 16/503,236

(22) Filed: Jul. 3, 2019

(65) Prior Publication Data

US 2019/0321649 A1 Oct. 24, 2019

Related U.S. Application Data

(60) Continuation of application No. 15/728,238, filed on Oct. 9, 2017, now Pat. No. 10,413,743, which is a
(Continued)

(51) Int. Cl.
*A61B 5/28* (2021.01)
*A61B 5/283* (2021.01)
(Continued)

(52) U.S. Cl.
CPC ............. *A61B 5/283* (2021.01); *A61B 5/363* (2021.01); *A61B 5/4836* (2013.01);
(Continued)

(58) Field of Classification Search
CPC ....... A61B 5/283; A61B 5/363; A61B 5/4836; A61N 1/0504; A61N 1/0563; A61N 1/3621; A61N 1/3622; A61N 1/3931
See application file for complete search history.

(56) References Cited

U.S. PATENT DOCUMENTS 4,787,389 A * 11/1988 Tarjan ................ A61N 1/39622
607/4
4,869,252 A 9/1989 Gilli
(Continued)

FOREIGN PATENT DOCUMENTS

AU 2015248172 B2 8/2017
CN 102462891 A 5/2012
(Continued)

OTHER PUBLICATIONS

"U.S. Appl. No. 14/620,862, Non Final Office Action dated Jan. 20, 2017", 9 Pgs.
(Continued)

*Primary Examiner* — Amanda K Hulbert
(74) *Attorney, Agent, or Firm* — Schwegman Lundberg & Woessner, P.A.

(57) ABSTRACT

In an example, an apparatus is described that includes an implantable housing, a heart signal sensing circuit configured to sense intrinsic electrical heart signals, a ventricular tachyarrhythmia (VT) detector circuit, operatively coupled to the heart signal sensing circuit, the detector circuit operable to detect a VT based on the sensed heart signals, a processor configured to control delivery of an anti-tachyarrhythmia pacing (ATP) therapy based on the detected VT, and an energy delivery circuit configured to deliver the ATP therapy in response to the detected VT, wherein the apparatus does not include a shock circuit capable of delivering a therapeutically-effective cardioverting or defibrillating shock.

16 Claims, 3 Drawing Sheets

Related U.S. Application Data division of application No. 14/620,862, filed on Feb. 12, 2015, now Pat. No. 9,782,601.

(60) Provisional application No. 61/979,634, filed on Apr. 15, 2014.

(51) Int. Cl.
| | | |
|---|---|---|
| *A61N 1/362* | (2006.01) | |
| *A61N 1/39* | (2006.01) | |
| *A61B 5/00* | (2006.01) | |
| *A61B 5/363* | (2021.01) | |
| *A61N 1/05* | (2006.01) | |

(52) U.S. Cl.
CPC ......... *A61N 1/3621* (2013.01); *A61N 1/3622* (2013.01); *A61N 1/3931* (2013.01); *A61N 1/0504* (2013.01); *A61N 1/0563* (2013.01)

(56) References Cited

U.S. PATENT DOCUMENTS

| | | | |
|---|---|---|---|
| 4,998,974 | A | 3/1991 | Aker |
| 5,372,606 | A | 12/1994 | Lang et al. |
| 5,411,525 | A | 5/1995 | Swanson et al. |
| 5,468,254 | A | 11/1995 | Hahn et al. |
| 5,634,938 | A | 6/1997 | Swanson et al. |
| 6,266,563 | B1 | 7/2001 | Kenknight et al. |
| 6,721,597 | B1 * | 4/2004 | Bardy ................ A61N 1/37512 128/898 |
| 6,885,890 | B2 | 4/2005 | Spinelli et al. |
| 7,386,344 | B2 | 6/2008 | Bocek et al. |
| 8,010,194 | B2 | 8/2011 | Muller |
| 8,306,620 | B2 | 11/2012 | Brown et al. |
| 8,744,572 | B1 | 6/2014 | Greenhut et al. |
| 9,782,601 | B2 | 10/2017 | Ludwig |
| 10,413,743 | B2 | 9/2019 | Ludwig |
| 2006/0036288 | A1 | 2/2006 | Bocek et al. |
| 2006/0206151 | A1 | 9/2006 | Lu |
| 2006/0265018 | A1 | 11/2006 | Smith et al. |
| 2006/0287681 | A1 | 12/2006 | Yonce et al. |
| 2007/0179538 | A1 | 8/2007 | Deno et al. |
| 2011/0098587 | A1 | 4/2011 | Haefner |
| 2015/0290467 | A1 | 10/2015 | Ludwig |
| 2018/0028829 | A1 | 2/2018 | Ludwig |

FOREIGN PATENT DOCUMENTS

| | | |
|---|---|---|
| CN | 106163611 B | 3/2019 |
| JP | 2008540040 A | 11/2008 |
| JP | 2012196485 A | 10/2012 |
| JP | 2013521816 A | 6/2013 |
| JP | 2013529508 A | 7/2013 |
| JP | 2017514570 A | 6/2017 |
| JP | 6542257 B2 | 6/2019 |
| WO | WO-2006020791 A1 | 2/2006 |
| WO | WO-2015160425 A1 | 10/2015 |

OTHER PUBLICATIONS

"U.S. Appl. No. 14/620,862, Notice of Allowance dated Jun. 7, 2017", 5 pgs.
"U.S. Appl. No. 14/620,862, Response filed Jan. 5, 2017 to Restriction Requirement dated Nov. 14, 2016", 6 pgs.
"U.S. Appl. No. 14/620,862, Response filed Apr. 17, 2017 to Non Final Office Action dated Jan. 20, 2017", 6 pgs.
"U.S. Appl. No. 14/620,862, Restriction Requirement dated Nov. 14, 2016", 6 pgs.
"U.S. Appl. No. 15/728,238, Notice of Allowance dated Jan. 17, 2019", 7 pgs.
"U.S. Appl. No. 15/728,238, Notice of Allowance dated May 6, 2019", 7 pgs.
"U.S. Appl. No. 15/728,238, Preliminary Amendment filed Nov. 7, 2017", 7 pgs.
"Australian Application Serial No. 2015248172, First Examiner Report dated Feb. 6, 2017", 3 pgs.
"Australian Application Serial No. 2015248172, Response filed Mar. 24, 2017 to First Examiner Report dated Feb. 6, 2017", 11 pgs.
"Chinese Application Serial No. 201580019480.9, Office Action dated Mar. 28, 2018", w/ English translation, 14 pgs.
"Chinese Application Serial No. 201580019480.9, Office Action dated Sep. 13, 2018", w/ English summary, 4 pgs.
"Chinese Application Serial No. 201580019480.9, Response filed Aug. 10, 2018 to Office Action dated Mar. 28, 2018", w/ English claims, 14 pgs.
"Chinese Application Serial No. 201580019480.9, Response filed Oct. 26, 2018 to Office Action dated Sep. 13, 2018", w/ English claims, 12 pgs.
"European Application Serial No. 15707214.1, Response filed May 26, 2017 to Communication Pursuant to Rules 161(1) and 162 EPC dated Nov. 22, 2016", 12 pgs.
"International Application Serial No. PCT/US2015/015614, International Preliminary Report on Patentability dated Oct. 27, 2016", 7 pgs.
"International Application Serial No. PCT/US2015/015614, International Search Report dated May 8, 2015", 4 pgs.
"International Application Serial No. PCT/US2015/015614, Written Opinion dated May 8, 2015", 5 pgs.
"Japanese Application Serial No. 2016-562770, Office Action dated May 29, 2018", W/ English Translation, 5 pgs.
"Japanese Application Serial No. 2016-562770, Office Action dated Sep. 26, 2017", with English translation, 15 pgs.
"Japanese Application Serial No. 2016-562770, Response filed Nov. 28, 2018 to Office Action dated May 29, 2018", w/ English claims, 6 pgs.
"Japanese Application Serial No. 2016-562770, Response filed Dec. 26, 2017 to Office Action dated Sep. 26, 2017", w/ claims in English, 9 pgs.
"European Application Serial No. 15707214.1, Communication Pursuant to Article 94(3) EPC dated Apr. 15, 2021", 4 pgs.
"European Application Serial No. 15707214.1, Response filed Jun. 21, 2021 to Communication pursuant to Article 94(3) EPC dated Apr. 15, 2021", 20 pgs.

\* cited by examiner

PACING DEVICE WITH AUTONOMOUS ANTI-TACHYCARDIA PACING

CLAIM OF PRIORITY

This application is a continuation of U.S. application Ser. No. 15/728,238, filed Oct. 9, 2017, which divisional of U.S. application Ser. No. 14/620,862, filed Feb. 12, 2015, now issued as U.S. Pat. No. 9,782,601, which claims the benefit of priority of U.S. Provisional Patent Application Ser. No. 61/979,634, titled "PACING DEVICE WITH AUTONOMOUS ANTI-TACHYCARDIA PACING" to Jacob M. Ludwig, and filed on Apr. 15, 2014, each of which is herein incorporated by reference in its entirety.

TECHNICAL FIELD

This disclosure relates generally to medical devices and more particularly, but not by way of limitation, to a pacing device.

BACKGROUND

The healthy heart produces regular, synchronized contractions. Rhythmic contractions of the heart are normally controlled by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and can be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia can quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

SUMMARY

In general, this disclosure describes techniques that allow a bradycardia pacing device to deliver anti-tachycardia pacing (ATP) and/or post shock pacing when implanted with a concomitant subcutaneous implantable cardioverter/defibrillator (S-ICD), for example. Using various techniques of this disclosure, the bradycardia pacing device may, for example, independently detect ventricular tachycardia (VT) and deliver anti-tachycardia pacing in response to the detected VT. Also, using various techniques of this disclosure, the bradycardia pacing device may include cardioversion/defibrillation shock detection capabilities and be configured to deliver post-shock pacing in response to detecting a shock.

In one aspect, this disclosure describes a system comprising a first device and a second device. The first device includes a first implantable housing, a plurality of subcutaneous electrodes configured to sense a plurality of electrical signals, a first processor configured to control delivery of a first cardiac electrical therapy based on the sensed electrical signals, and a first energy delivery circuit configured to deliver shock therapy. The second device includes a second implantable housing, a heart signal sensing circuit configured to sense intrinsic electrical heart signals, a ventricular tachyarrhythmia (VT) detector circuit, operatively coupled to the heart signal sensing circuit, the VT detector circuit operable to detect a VT based on the sensed heart signals, a second processor configured to control delivery of an anti-tachyarrhythmia pacing (ATP) therapy based on the detected VT, and a second energy delivery circuit configured to deliver the ATP therapy.

In another aspect, this disclosure describes an apparatus comprising an implantable housing, a heart signal sensing circuit configured to sense intrinsic electrical heart signals, a ventricular tachyarrhythmia (VT) detector circuit, operatively coupled to the heart signal sensing circuit, the detector circuit operable to detect a VT based on the sensed heart signals, a processor configured to control delivery of an anti-tachyarrhythmia pacing (ATP) therapy based on the detected VT, and an energy delivery circuit configured to deliver the ATP therapy in response to the detected VT, wherein the apparatus does not include a shock circuit capable of delivering a therapeutically-effective cardioverting or defibrillating shock.

In another aspect, this disclosure is directed to a system comprising a first device and a second device. The first device includes a first implantable housing, a plurality of subcutaneous electrodes configured to sense a plurality of electrical signals, a first processor configured to control delivery of a defibrillation shock therapy based on the sensed electrical signals, and a first energy delivery circuit configured to deliver the shock therapy. The second device includes a second implantable housing, a heart signal sensing circuit configured to sense intrinsic electrical heart signals, a shock detector circuit, operatively coupled to the heart signal sensing circuit, the shock detector circuit operable to detect the delivery of shock therapy, a second processor configured to control delivery of a post-shock pacing therapy based on the detected delivery of shock therapy, and a second energy delivery circuit configured to deliver the post-shock pacing therapy.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Currently, a bradycardia patient may receive a pacemaker to treat a slow heart rhythm condition. A typical pacemaker, however, does not include anti-tachycardia pacing (ATP) capabilities because it may be undesirable to perform ATP therapy without a backup shock capability, due to the possibility of acceleration. Without a shock therapy capability as a backup, a life-threatening condition may result if ATP therapy was unsuccessful, or if the ATP therapy drove the heart into fibrillation. As a result, if the bradycardia patient began experiencing fibrillation, the patient's existing options include receiving a pacemaker with implantable cardioverter/defibrillator (ICD) capabilities. However, this would mean that the patient's existing pacemaker needs to be replaced with a pacemaker/ICD device, and a high-voltage lead needs to be implanted, both of which are undesirably invasive procedures.

Another existing option for the patient is to receive a subcutaneous implantable cardioverter/defibrillator (S-ICD). Existing S-ICD devices, however, do not offer ATP therapy, which when delivered to convert a fibrillation can cause less discomfort to the patient than shock therapy. In addition, existing S-ICD devices may deliver post-shock pacing via the same vector as shock therapy, which may capture a significant amount of the muscle in a patient's upper torso. This amount of muscle capture may cause patient discomfort.

This disclosure describes, among other things, techniques that may allow a bradycardia device, co-implanted with an S-ICD device, to deliver ATP and/or post-shock pacing. In accordance with this disclosure, and as described in more detail below, the bradycardia device of this disclosure may include ATP therapy capabilities, which may be turned on when co-implanted with an S-ICD. In addition, the delivery of ATP or post-shock pacing may be handled autonomously by the bradycardia device, e.g., not in response to a communicated request from another device such as the S-ICD device. In other words, using various techniques of this disclosure, the bradycardia device itself may be capable of detecting an arrhythmia and delivering ATP, or detecting a shock and delivering post-shock therapy on its own.

Figure 1:
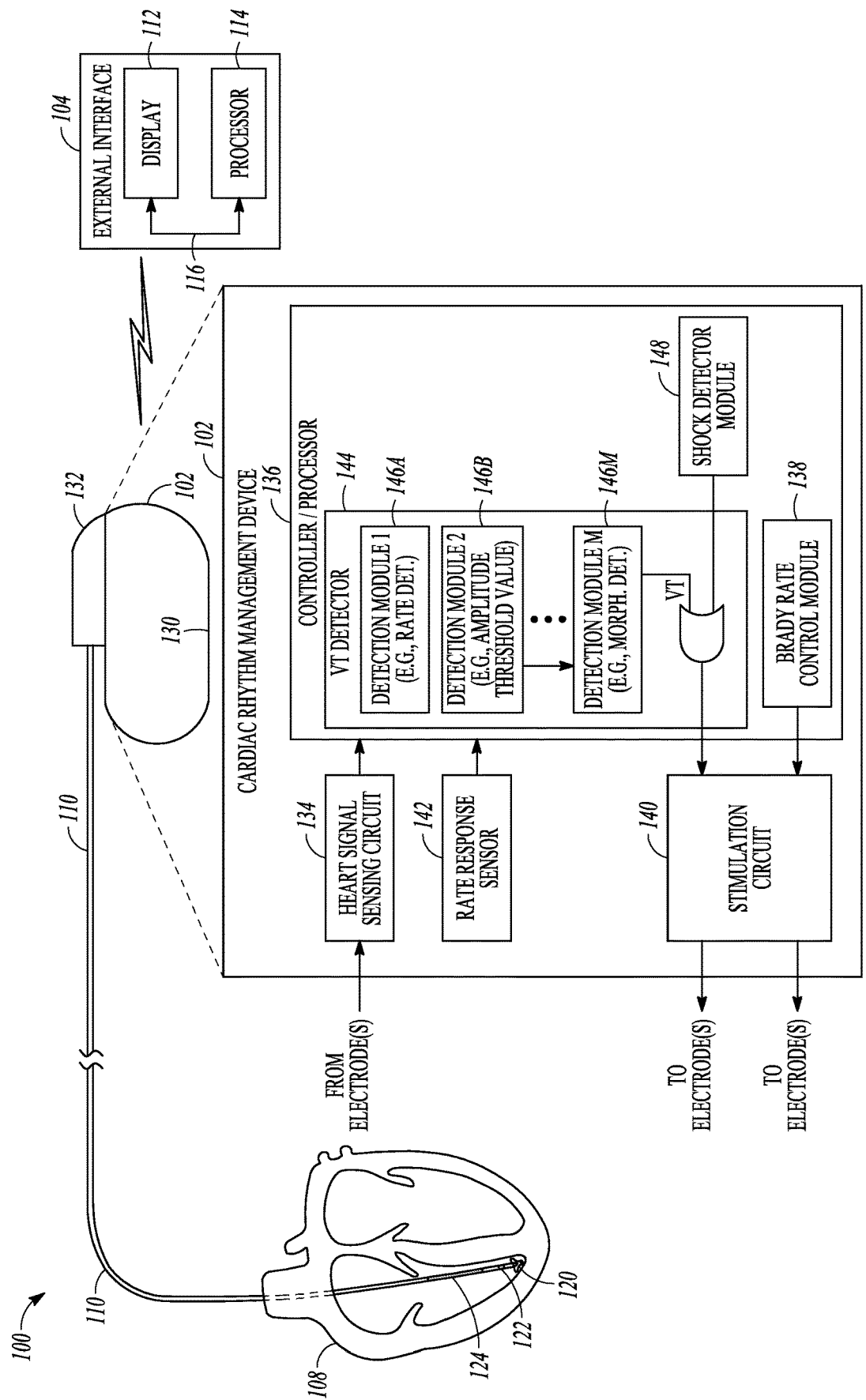
FIG. 1 is a schematic diagram illustrating details of one example of portions of a bradycardia system that may be used to implement various techniques of this disclosure.

FIG. 1 is a schematic diagram illustrating details of one example of portions of a bradycardia system that may be used to implement various techniques of this disclosure. In this example configuration, the system 100 includes an implantable bradycardia device 102 (also referred to in this disclosure as "brady device 102"). The system 100 may also include a programmer or other external interface device 104 permitting wireless or other communication with the device 102. The device 102 may be implanted in a pectoral region of a patient. The device 102 in this example may include an electronics unit that is coupled to the patient's heart 108, such as by one or more intravascular or other leads 110. Each such lead 110 typically includes one or more electrodes for contacting a desired location within the patient 106, such as for sensing one or more intrinsic electrical heart signals or for delivering one or more pacing stimulations.

In this example, a distal portion of the lead 110 is located in a right ventricle of the heart 108 and includes one or more electrodes such as a distal tip electrode 120, a slightly more proximal ring electrode 122, and an even slightly more proximal coil or other shock electrode 124. However, the system 100 may additionally or alternatively include other leads or electrodes that may be located elsewhere in or near the heart 108. The device 102 typically includes electronics carried in a hermetically-sealed "can" 130. The can 130 typically includes one or more feedthroughs to a header 132. The header 132 typically includes one or more receptacles for receiving a proximal portion of one or more of the leads 110. One or both of the can 130 or header 132 may also include additional electrodes, such as for sensing intrinsic heart or other signals or for delivering stimulation or other energy to the patient 106.

The electronics unit of the device 102 typically includes a heart signal sensing circuit 134 to sense intrinsic electrical heart signals, such as depolarizations indicative of heart contractions. Such heart signals also include information about cardiac arrhythmias, such as ventricular tachycardia (VT). The heart signal sensing circuit 134 typically includes one or more sense amplifier circuits to detect the heart signals, one or more filters for emphasizing depolarizations or other desired information, or for attenuating undesired information. In one example, the heart signal sensing circuit 134 also includes one or more peak or level detectors for detecting occurrences of heart depolarizations and providing corresponding responsive depolarization interrupts to a micro-processor or other controller 136.

The controller 136 may include dedicated hardware or executable instructions to provide its functionality, such as to time the intervals between like depolarizations to determine a heart rate. In one example, the controller 136 includes a bradyarrhythmia rate control module 138 to determine whether the heart 108 needs a pacing-level electrical stimulation to induce or spatially coordinate a resulting heart contraction. The bradyarrhythmia rate control module 138 delivers one or more control signals to an energy deliver circuit, namely stimulation circuit 140, based on one or more operational parameters, e.g., pacing rate and voltage level. In response, the stimulation circuit 140 is configured to deliver electrical energy via the electrodes to the heart 108 to evoke or assist in evoking or coordinating a responsive heart contraction. The bradyarrhythmia rate control module 140 typically receives information from a rate response sensor 142 (e.g., accelerometer, minute ventilation, etc.) to indicate the patient's metabolic need for a particular heart rate and corresponding cardiac output.

The controller 136 may also include a VT detector 144 that is operatively coupled to the heart signal sensing circuit 134, configured to detect a VT based on the sensed heart signals, and autonomously determine whether to deliver ATP pacing if VT is present. That is, the controller 136 of a brady device 102 that is co-implanted with an S-ICD device is capable of detecting an arrhythmia and controlling delivery of ATP therapy, e.g., via stimulation circuit 140, without receiving a communicated request from the S-ICD device. Thus, the brady device 102 may autonomously handle the delivery of ATP therapy. By eliminating a communication requirement between the brady device 102 and an S-ICD device, for example, the techniques of this disclosure may be advantageously compatible across device manufacturers.

It may be undesirable to provide ATP therapy without the ability to deliver backup defibrillation therapy. If a patient has a tachyarrhythmia and ATP therapy is delivered, it may drive the tachyarrhythmia into fibrillation, a potentially life-threatening condition. As such, in one example implementation, the brady device 102, which does not include the capability to deliver shock therapy, may be programmable such that ATP therapy is only available for delivery if an S-ICD device is present in the patient. For example, a physician implanting the brady device 102 knows whether the patient has an S-ICD device already implanted. If so, then the physician may enable the ATP therapy functionality of the brady device 102.

The physician may, for example, enable the ATP therapy functionality of the brady device 102 using the programmer 104. For example, the programmer 104 may transmit one or more operational parameters, e.g., pacing rate and voltage level, to the brady device 102. In some examples, the one or more ATP therapy operational parameters, e.g., pacing rate and voltage level, are different than those used by the bradyarrhythmia rate control module 138 to deliver brady therapy, e.g., therapy that is neither ATP therapy nor post-shock pacing therapy.

In addition, the programmer 104 may transmit "enable" or "disable" parameters to the brady device 102 that either allow or inhibit the delivery of ATP therapy, respectively. The brady device 102 may store the received parameters, for example, in a memory device (not depicted). Upon detecting a VT, the controller 136 may determine that the ATP therapy is enabled based on the stored parameters and proceed to deliver ATP therapy.

If the patient were to have the S-ICD device removed, the physician may disable the ATP therapy functionality of the brady device 102 using the programmer 104. For example, the programmer 104 may transmit parameters to the brady device 102. The brady device 102 may store the received parameters, for example, in a memory device (not depicted). Upon detecting a VT, the controller 136 may determine that the ATP therapy is disabled based on the stored parameters and, as such, not deliver ATP therapy.

The determination of whether VT is present is typically performed by one or more VT detection modules 146A-M (collectively referred to in this disclosure as "detection modules 146"). Each detection module 146 typically includes its own particular criterion, criteria, or technique(s) for determining whether VT is present.

In one example, the VT detector 144 includes a rate detector module 146A. In one example, the rate detector module 146A deems a VT arrhythmia to be present if a detected heart rate exceeds a high rate threshold value, such as a high rate threshold value that is in a range between about 150 beats per minute and about 250 beats per minute. In one example, the high rate threshold value is equal to 220 beats per minute. Therefore, in this example, only heart rhythms with a heart rate that exceeds 220 beats per minute will be deemed a VT arrhythmia by such a detection module 146A. The particular high rate threshold value of the rate detector of detection module 146A can be programmably adjusted to a higher or lower value to obtain (or to help obtain) the desired specificity.

In another example, a sensing control detection module 146B is used to control how ventricular depolarizations are sensed by the heart signal sensing circuit 134, such as to increase the specificity of detecting a ventricular tachyarrhythmia. In one example, the sensing control detection module 146B establishes a higher amplitude level-detection threshold on the intrinsic ventricular cardiac signal sensed by the heart signal sensing circuit 134 for declaring the detection of a ventricular depolarization. For example, a typical ventricular depolarization level-detection threshold is set at about 0.3 mV. When the intrinsic cardiac signal exceeds 0.3 mV, a detected ventricular depolarization is declared. However, for the present increased VT arrhythmia specificity, the ventricular depolarization level-detection threshold is instead set between about 0.6 mV and 2.5 mV, such as at about 1.1 mV, such that a detected ventricular depolarization is declared only when the intrinsic ventricular cardiac signal level exceeds the threshold value (e.g., 1.1 mV). This improves noise rejection of spurious myopotentials and other noise. This increases the specificity of detecting ventricular depolarizations, which, in turn, increases the specificity of detecting and declaring a VT arrhythmia. In one example, the actual ventricular depolarization amplitude level-detection threshold value is established by sensing the noise floor of the intrinsic ventricular cardiac signal, and then setting the amplitude level-detection threshold value above the sensed noise floor.

In another example, the one or more detection modules 146 include a morphology detection module 146M. In one example, the morphology detection module 146M compares a morphology of the detected heart signal against a template morphology, such as to classify whether a detected heart rhythm is a VT rhythm that should be shocked. In one example, one or more parameters of such a morphology detection module 146M is adjusted to obtain (or to help obtain) the desired specificity. An example of such a parameter would be a correlation coefficient threshold value, where a correlation coefficient between the detected heart rhythm and the template morphology is computed and compared to the threshold value.

In general, there are many types of detection modules 146 that can be used to detect a ventricular arrhythmia such as VT, and the various operative parameters of such modules can be programmed to obtain the desired specificity. Moreover, such detection modules 146 can be used conjunctively to further increase specificity, such as to obtain a specificity that exceeds the sensitivity. Thus, the rate and morphology detectors discussed above are merely representative illustrative examples of the types of detection modules 146 that can be used in the present system 100.

In one example, ATP therapy parameters may be programmable, e.g., by a physician or other clinician. For example, a physician may use programmer 104 to transmit one or more ATP therapy parameters to the brady device 102. In some example implementations, the brady device 102 may be programmed such that the ATP therapy is delivered with a bipolar pacing vector, such that any sensing by the S-ICD device would not be adversely affected (in contrast to a unipolar pacing vector, for example). In one example implementation, one or more VT detection parameters may be programmed to ensure that the programming of the brady device 102, e.g., VT thresholds, align with the programming of the S-ICD device.

As mentioned above, using various techniques of this disclosure, the bradycardia pacing device 102 may additionally or alternatively be configured to autonomously determine whether to deliver post-shock pacing therapy in response to detecting delivery of a cardioversion/defibrillation shock. That is, the controller 136 of the brady device 102 that is co-implanted with an S-ICD device may be capable of detecting that a cardioversion/defibrillation shock was delivered by the S-ICD device and, in response, control delivery of post-shock pacing therapy without receiving a communicated request from the S-ICD device. Thus, the brady device 102 may autonomously handle the delivery of post-shock pacing therapy.

Because the brady device 102 is not configured to deliver cardioversion or defibrillation shock therapy, in order to deliver post-shock pacing, the brady device 102 should be configured to detect that the co-implanted S-ICD device has delivered a shock. In one example, the brady device 102 includes a shock detector module 148.

In one example implementation, the shock detector module 148 may determine that a shock has been delivered by the S-ICD device by monitoring one or more sense channels of the heart signal sensing circuit 134. For example, the shock detector module 148 may monitor one or more sense channels of the heart signal sensing circuit 134 and determine that a shock has been delivered if a large deviation in voltage occurs. Upon determining that a shock has been delivered, the brady device 102 may begin delivering post-shock pacing therapy.

In another example implementation, the shock detector module 148 may include a surge suppressor, or be in communication with a surge suppressor. The surge suppressor may turn on when it detects a large voltage, e.g., on the sense channels, which is indicative of delivery of a shock. Upon detecting that the surge suppressor has turned on, the shock detector module 148 may determine that a shock has been delivered and, as such, the controller 136 may begin controlling delivery of post-shock pacing therapy via stimulation circuit 140.

In some example implementations, the shock detector module 148 may include circuitry dedicated to shock detection. For example, the shock detector module 148 may include circuitry that detects and determines a voltage differential between two electrodes. Based on the voltage difference, the shock detector module 148 may determine that a shock has been delivered and, as such, the brady device 102 may begin delivering post-shock pacing therapy.

In one example, the post-shock pacing therapy may be programmable, e.g., by a physician or other clinician. For example, the programmer 104 may transmit one or more operational parameters, e.g., pacing rate and voltage level, to the brady device 102. In some examples, the one or more post-shock pacing therapy operational parameters, e.g., pacing rate and voltage level, are different than those used by the bradyarrhythmia rate control module 138 to delivery brady therapy, e.g., therapy that is neither ATP therapy nor post-shock pacing therapy.

In addition, the programmer 104 may transmit enable or disable parameters to the brady device 102 that either allow or inhibit the delivery of post-shock pacing therapy. The physician may, for example, enable the post-shock pacing therapy functionality of the brady device 102 by using the programmer 104 to transmit one or more parameters that enable delivery of post-shock pacing therapy by the brady device 102. The brady device 102 may store the received parameters, for example, in a memory device (not depicted). Upon detecting a shock, the controller 136 may determine that the post-shock pacing therapy is enabled based on the stored parameters and proceed to deliver post-shock pacing therapy. Additionally, a physician may use programmer 104 to transmit one or more post-shock pacing therapy parameters to the brady device 102, e.g., pacing rate, etc.

In addition to the techniques described above, the brady device 102 may inhibit or stop delivery of ATP therapy if the shock detector module 148 determines that a shock has been delivered. For example, if an S-ICD device delivers shock therapy prior to or during the delivery of ATP therapy by the brady device 102, the brady device 102 may abort the ATP therapy. As mentioned above, shock detector module 148 may use dedicated circuitry or a surge suppressor, for example, to determine that a shock has been delivered.

Figure 2:
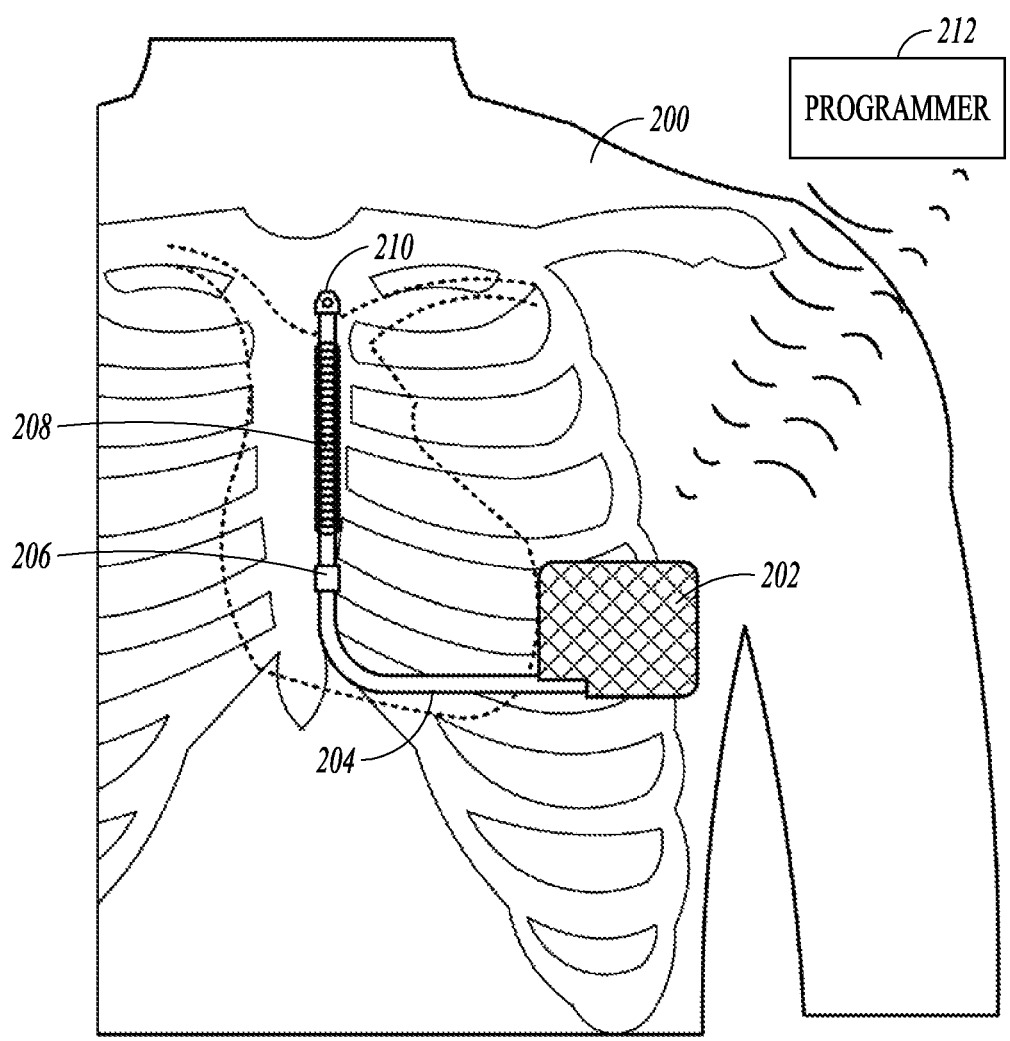
FIG. 2 illustrates a possible position of a subcutaneous implantable cardioverter/defibrillator (S-ICD) system.

FIG. 2 illustrates a possible position of a subcutaneous implantable cardioverter/defibrillator (S-ICD) system. The example system is implanted in a patient 200, over the patient's ribs and beneath the skin. An S-ICD device 202 is implanted, in the example, at approximately the left axilla (armpit), beneath the arm. A lead 204 extends from the S-ICD device 202 toward the patient's xiphoid and then over or slightly to the left of the sternum. The lead 204 includes electrodes 206, 208 and 210, with electrode 208 illustrated as a coil electrode designed primarily for shock delivery (though sensing via coil electrode 208 may be performed as well). The other electrodes 206 and 210 on lead 204 are shown as ring and cap electrodes, respectively. Other designs may be used. The S-ICD device 202, includes a housing having, in this example, a conductive surface or, if desired, has an area on its surface which is conductive to allow for at least sensing of electrical signals and, when needed, therapy delivery.

Other configurations and implant locations may be used instead. Examples include right-sided or anterior-posterior subcutaneous implantation, transvenous systems, epicardial systems, intravascular systems, and other implementations such as drug pumps or neurostimulation systems that may incorporate cardiac signal analysis.

A programmer or other external interface device 212 permits wireless or other communication with the device 202. In some example configurations, the programmer 212 and the programmer 104 of FIG. 1 may be the same device.

Figure 3:
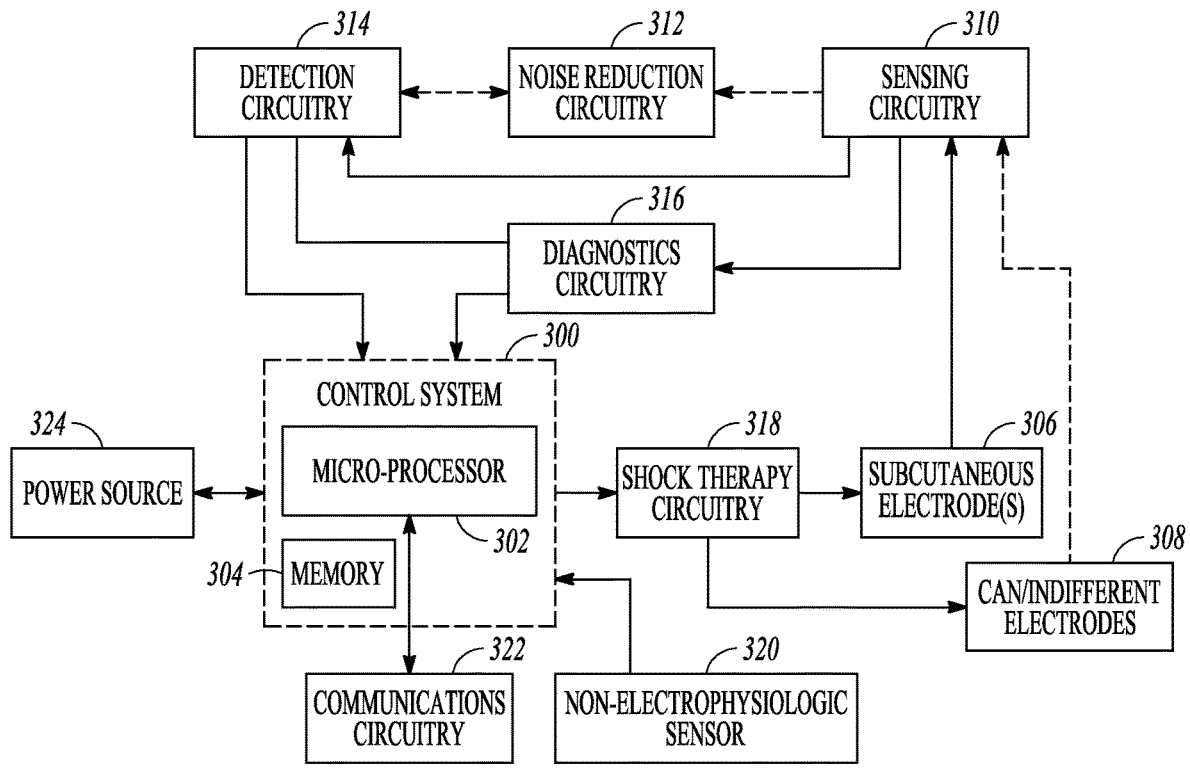
FIG. 3 is a block diagram illustrating various components of an S-ICD that may be used to in accordance with this disclosure

FIG. 3 is a block diagram illustrating various components of an S-ICD device, e.g., S-ICD device 202 of FIG. 2, that may be used to in accordance with this disclosure. The S-ICD device incorporates a processor-based control system 300 that includes a micro-processor 302 coupled to appropriate memory (volatile and non-volatile) 304, it being understood that any logic-based control architecture may be used. The control system 300 is coupled to circuitry and components to sense, detect, and analyze electrical signals produced by the heart and deliver electrical stimulation energy to the heart under predetermined conditions to treat cardiac arrhythmias. The electrical energy delivered by the S-ICD may be in the form of high-energy pulses for cardioversion or defibrillation.

Cardiac signals are sensed using the subcutaneous electrode(s) 306 and the can or indifferent electrode 308 provided on the S-ICD housing. Cardiac signals may also be sensed using only the subcutaneous electrodes 306, such as in a non-active can configuration. As such, unipolar, bipolar, or combined unipolar/bipolar electrode configurations as well as multi-element electrodes and combinations of noise canceling and standard electrodes may be employed. The sensed cardiac signals are received by sensing circuitry 310, which includes sense amplification circuitry and may also include filtering circuitry and an analog-to-digital (A/D) converter. The sensed cardiac signals processed by the sensing circuitry 310 may be received by noise reduction circuitry 312, which may further reduce noise before signals are sent to the detection circuitry 314. Noise reduction circuitry 312 may also be incorporated after sensing circuitry 310 in cases where high power or computationally intensive noise reduction algorithms are required.

Detection circuitry 314 typically includes a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 314 to detect and verify the presence and severity of an arrhythmic episode.

The detection circuitry 314 communicates cardiac signal information to the control system 300. Memory circuitry 304 of the control system 300 contains parameters for operating in various sensing and defibrillation modes, and stores data indicative of cardiac signals received by the detection circuitry 314. The memory circuitry 304 may also be configured to store historical ECG and therapy data, which may be used for various purposes and transmitted to an external receiving device as needed or desired.

In certain configurations, the S-ICD may include diagnostics circuitry 316. The diagnostics circuitry 316 typically receives input signals from the detection circuitry 314 and the sensing circuitry 310. The diagnostics circuitry 316 provides diagnostics data to the control system 300, it being understood that the control system 300 may incorporate all or part of the diagnostics circuitry 316 or its functionality.

According to a configuration that provides cardioversion and/or defibrillation therapies, the control system 300 processes cardiac signal data received from the detection circuitry 314 and initiates appropriate tachyarrhythmia therapies to terminate cardiac arrhythmic episodes and return the heart to normal sinus rhythm. The control system 300 is coupled to an energy delivery circuit, namely shock therapy circuitry 318. The shock therapy circuitry 318 is coupled to the subcutaneous electrode(s) 306 and the can or indifferent electrode 308 of the S-ICD housing. Upon command, the shock therapy circuitry 318 delivers cardioversion and defibrillation stimulation energy to the heart in accordance with a selected cardioversion or defibrillation therapy. Example configurations of ICD high energy delivery circuitry, structures and functionality, aspects of which may be incorporated in an S-ICD of a type that may benefit from aspects of the present invention are disclosed in commonly owned U.S. Pat. Nos. 5,372,606; 5,411,525; 5,468,254; and 5,634,938, which are hereby incorporated herein by reference in their respective entireties.

The S-ICD shown in FIG. 3 is configured to receive signals from one or more physiologic and/or non-physiologic sensors in accordance with embodiments of the present invention. Non-electrophysiological cardiac sensors 320 may be coupled directly to the detection circuitry 314 or indirectly via the sensing circuitry 310. Non-electrophysiological cardiac sensors 320 sense cardiac activity that is non-electrophysiological in nature. Examples of non-electrophysiological cardiac sensors are blood oxygen sensors, blood volume sensors, acoustic sensors and/or pressure transducers, and accelerometers. Signals from these sensors are developed based on cardiac activity, but are not derived directly from electrophysiological sources (e.g., R-waves or P-waves).

Communications circuitry 322 is coupled to the microprocessor 302 of the control system 300. The communications circuitry 322 may allow the S-ICD to communicate with an external programmer.

Typically, the S-ICD is encased and hermetically sealed in a housing suitable for implanting in a human body as is known in the art. Power to the S-ICD is supplied by a power source 324 housed within the S-ICD.

Figure 4:
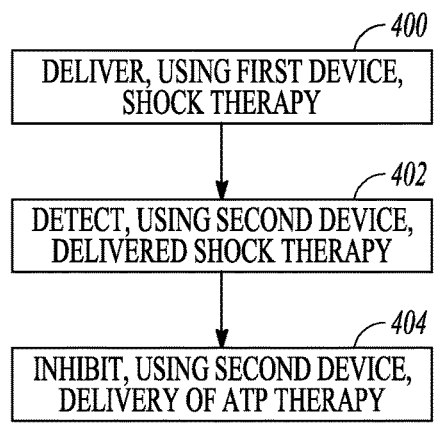
FIG. 4 is an example of a method that may be used to implement various techniques of this disclosure.

FIG. 4 is an example of a method that may be used to implement various techniques of this disclosure. In the method shown in FIG. 4, a first device, e.g., S-ICD 202 of FIG. 2, delivers a shock therapy, e.g., using shock therapy circuitry 318 of FIG. 3 (block 400). A second device, e.g., the brady device 102 of FIG. 1, detects the delivered shock therapy, e.g., using shock detector module 148 (block 402). In response to detecting the delivered shock therapy, the second device, e.g., the brady device 102, inhibits or stops delivering ATP therapy (block 404).

Figure 5:
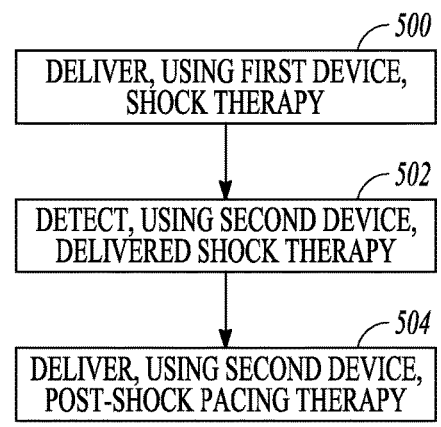
FIG. 5 is an example of another method that may be used to implement various techniques of this disclosure.

FIG. 5 is an example of another method that may be used to implement various techniques of this disclosure. In the method shown in FIG. 5, a first device, e.g., S-ICD 202 of FIG. 2, delivers a shock therapy, e.g., using shock therapy circuitry 318 of FIG. 3 (block 500). A second device, e.g., the brady device 102 of FIG. 1, detects the delivered shock therapy, e.g., using shock detector module 148 (block 502). In response to detecting the delivered shock therapy, the second device, e.g., the brady device 102, delivers a post-shock pacing therapy (block 504).

VARIOUS NOTES AND EXAMPLES

Modules and other circuitry shown and described herein may be implemented using software, hardware, firmware and/or combinations thereof. Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods.

Example 1 includes subject matter (such as a device, apparatus, or machine) that may comprise: a first device including: a first implantable housing; a plurality of subcutaneous electrodes configured to sense a plurality of electrical signals; a first processor configured to control delivery of a first cardiac electrical therapy based on the sensed electrical signals; a first energy delivery circuit configured to deliver shock therapy; and a second device including: a second implantable housing; a heart signal sensing circuit configured to sense intrinsic electrical heart signals; a ventricular tachyarrhythmia (VT) detector circuit, operatively coupled to the heart signal sensing circuit, the VT detector circuit operable to detect a VT based on the sensed heart signals; a second processor configured to control delivery of an anti-tachyarrhythmia pacing (ATP) therapy based on the detected VT; and a second energy delivery circuit configured to deliver the ATP therapy.

In Example 2, the subject matter of Example 1 may include, wherein the second processor is configured to control delivery of the ATP therapy without a communicated request from the first device.

In Example 3, the subject matter of one or more of Examples 1 and 2 may include, wherein the second device is configured to receive at least one ATP therapy parameter, and wherein the second processor is configured to enable or disable the delivery of the ATP therapy based on the at least one received ATP therapy parameter.

In Example 4, the subject matter of one or more of Examples 1-3 may include, wherein the second device comprises a shock detection module to detect delivery of the shock therapy.

In Example 5, the subject matter of Example 4 may include, wherein the second processor is configured to inhibit or stop delivery of the ATP therapy when the shock detection module detects delivery of the shock therapy.

In Example 6, the subject matter of any one of Examples 4 to 5 may include, wherein the second device is configured to receive at least one post-shock pacing therapy parameter, and wherein the second processor is configured to control the delivery of the post-shock pacing therapy based on the at least one received post-shock pacing therapy parameter.

In Example 7, the subject matter of any one of Examples 4 to 6 may include, wherein the second device is configured to receive at least one post-shock pacing therapy parameter, and wherein the second processor is configured to enable or disable the delivery of the post-shock pacing therapy based on the at least one received post-shock pacing therapy parameter.

Example 8 includes subject matter (such as a device, apparatus, or machine) that may comprise: an implantable housing; a heart signal sensing circuit configured to sense intrinsic electrical heart signals; a ventricular tachyarrhythmia (VT) detector circuit, operatively coupled to the heart signal sensing circuit, the detector circuit operable to detect a VT based on the sensed heart signals; a processor configured to control delivery of an anti-tachyarrhythmia pacing (ATP) therapy based on the detected VT; and an energy delivery circuit configured to deliver the ATP therapy in response to the detected VT, wherein the apparatus does not include a shock circuit capable of delivering a therapeutically-effective cardioverting or defibrillating shock.

In Example 9, the subject matter of Example 8 may include, wherein the processor is configured to control delivery of the ATP therapy without a communicated request from another implanted device.

In Example 10, the subject matter of any one of Examples 8 and 9 may include, wherein the processor is configured to receive at least one ATP therapy parameter, and wherein the processor is configured to enable or disable the delivery of the ATP therapy based on the at least one received ATP therapy parameter.

In Example 11, the subject matter of any one of Examples 8-10 may include, a shock detection module to detect delivery of the shock therapy.

In Example 12, the subject matter of Example 11 may include, wherein the processor is configured to inhibit or stop delivery of the ATP therapy when the shock detection module detects delivery of the shock therapy.

In Example 13, the subject matter of any one of Examples 11 to 12 may include, wherein the processor is configured to receive at least one post-shock pacing therapy parameter, and wherein the processor is configured to control the delivery of the post-shock pacing therapy based on the at least one post-shock pacing therapy parameter.

In Example 14, the subject matter of any one of Examples 11 to 13 may include, wherein the processor is configured to receive at least one post-shock pacing therapy parameter, and wherein the processor is configured to enable or disable the delivery of the post-shock pacing therapy based on the at least one received post-shock pacing therapy parameter.

Example 15 includes subject matter (such as a device, apparatus, or machine) that may comprise: a first device including: a first implantable housing; a plurality of subcutaneous electrodes configured to sense a plurality of electrical signals; a first processor configured to control delivery of a defibrillation shock therapy based on the sensed electrical signals; a first energy delivery circuit configured to deliver the shock therapy; and a second device including: a second implantable housing; a heart signal sensing circuit configured to sense intrinsic electrical heart signals; a shock detector circuit, operatively coupled to the heart signal sensing circuit, the shock detector circuit operable to detect the delivery of shock therapy; a second processor configured to control delivery of a post-shock pacing therapy based on the detected delivery of shock therapy; and a second energy delivery circuit configured to deliver the post-shock pacing therapy.

Example 16 includes subject matter (such as a device, apparatus, or machine) that may comprise: a first device including: a first implantable housing; a plurality of subcutaneous electrodes configured to sense a plurality of electrical signals; a first processor configured to control delivery of a first cardiac electrical therapy based on the sensed electrical signals; a first energy delivery circuit configured to deliver shock therapy; and a second device including: a second implantable housing; a heart signal sensing circuit configured to sense intrinsic electrical heart signals; a ventricular tachyarrhythmia (VT) detector circuit, operatively coupled to the heart signal sensing circuit, the VT detector circuit operable to detect a VT based on the sensed heart signals; a second processor configured to control delivery of an anti-tachyarrhythmia pacing (ATP) therapy based on the detected VT; and a second energy delivery circuit configured to deliver the ATP therapy.

In Example 17, the subject matter of Example 16 may include, wherein the second processor is configured to control delivery of the ATP therapy without a communicated request from the first device.

In Example 18, the subject matter of any one of Examples 16 to 17 may include, wherein the second device is configured to receive at least one ATP therapy parameter, and wherein the second processor is configured to enable or disable the delivery of the ATP therapy based on the at least one received ATP therapy parameter.

In Example 19, the subject matter of any one of Examples 16 to 18 may include, wherein the second device comprises: a shock detection module to detect delivery of the shock therapy.

In Example 20, the subject matter of any one of Examples 16 to 19 may include, wherein the second processor is configured to inhibit or stop delivery of the ATP therapy when the shock detection module detects delivery of the shock therapy.

In Example 21, the subject matter of any one of Examples 16 to 20 may include, wherein the second device is configured to receive at least one post-shock pacing therapy parameter, and wherein the second processor is configured to control the delivery of the post-shock pacing therapy based on the at least one received post-shock pacing therapy parameter.

In Example 22, the subject matter of any one of Examples 16 to 21 may include, wherein the second device is configured to receive at least one post-shock pacing therapy parameter, and wherein the second processor is configured to enable or disable the delivery of the post-shock pacing therapy based on the at least one received post-shock pacing therapy parameter.

Example 23 includes subject matter (such as a device, apparatus, or machine) that may comprise: an implantable housing; a heart signal sensing circuit configured to sense intrinsic electrical heart signals; a ventricular tachyarrhythmia (VT) detector circuit, operatively coupled to the heart signal sensing circuit, the detector circuit operable to detect a VT based on the sensed heart signals; a processor configured to control delivery of an anti-tachyarrhythmia pacing (ATP) therapy based on the detected VT; and an energy delivery circuit configured to deliver the ATP therapy in response to the detected VT, wherein the apparatus does not include a shock circuit capable of delivering a therapeutically-effective cardioverting or defibrillating shock.

In Example 24, the subject matter of Example 23 may include, wherein the processor is configured to control delivery of the ATP therapy without a communicated request from another implanted device.

In Example 25, the subject matter of any one of Examples 23 to 24 may include, wherein the processor is configured to receive at least one ATP therapy parameter, and wherein the processor is configured to enable or disable the delivery of the ATP therapy based on the at least one received ATP therapy parameter.

In Example 26, the subject matter of any one of Examples 23 to 25 may include, a shock detection module to detect delivery of the shock therapy.

In Example 27, the subject matter of any one of Examples 23 to 26 may include, wherein the processor is configured to inhibit or stop delivery of the ATP therapy when the shock detection module detects delivery of the shock therapy.

In Example 28, the subject matter of any one of Examples 23 to 27 may include, wherein the processor is configured to receive at least one post-shock pacing therapy parameter, and wherein the processor is configured to control the delivery of the post-shock pacing therapy based on the at least one post-shock pacing therapy parameter.

In Example 29, the subject matter of any one of Examples 23 to 28 may include, wherein the processor is configured to receive at least one post-shock pacing therapy parameter, and wherein the processor is configured to enable or disable the delivery of the post-shock pacing therapy based on the at least one received post-shock pacing therapy parameter.

Example 30 includes subject matter (such as a device, apparatus, or machine) that may comprise: a first device including: a first implantable housing; a plurality of subcutaneous electrodes configured to sense a plurality of electrical signals; a first processor configured to control delivery of a defibrillation shock therapy based on the sensed electrical signals; a first energy delivery circuit configured to deliver the shock therapy; and a second device including: a second implantable housing; a heart signal sensing circuit configured to sense intrinsic electrical heart signals; a shock detector circuit, operatively coupled to the heart signal sensing circuit, the shock detector circuit operable to detect the delivery of shock therapy; a second processor configured to control delivery of a post-shock pacing therapy based on the detected delivery of shock therapy; and a second energy delivery circuit configured to deliver the post-shock pacing therapy.

In Example 31, the subject matter of Example 30 may include, wherein the second processor is configured to control delivery of the post-shock pacing therapy without a communicated request from the first device.

In Example 32, the subject matter of any one of Examples 30 to 31 may include, wherein the second device is configured to receive at least one post-shock pacing therapy parameter, and wherein the second processor is configured to control the delivery of the post-shock pacing therapy based on the at least one received post-shock pacing therapy parameter.

In Example 33, the subject matter of any one of Examples 30 to 32 may include, wherein the second device is configured to receive at least one post-shock pacing therapy parameter, and wherein the second processor is configured to enable or disable the delivery of the post-shock pacing therapy based on the at least one received post-shock pacing therapy parameter.

In Example 34, the subject matter of any one of Examples 30 to 33 may include, wherein the second device comprises: a ventricular tachyarrhythmia (VT) detector circuit, operatively coupled to the heart signal sensing circuit, the VT detector circuit operable to detect a VT based on the sensed heart signals, wherein the second processor is configured to control delivery of an anti-tachyarrhythmia pacing (ATP) therapy based on the detected VT, and wherein the second energy delivery circuit is configured to deliver the ATP therapy.

In Example 35, the subject matter of any one of Examples 30 to 34 may include, wherein the second processor is configured to inhibit or stop delivery of the ATP therapy when the shock detection module detects delivery of the shock therapy.

Each of these non-limiting examples can stand on its own, or can be combined in various permutations or combinations with one or more of the other examples.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

The invention claimed is:

1. A system comprising:
   a first implantable device configured to receive first electrical heart signals from at least one subcutaneous electrode, the first implantable device comprising:
   a first processor configured to control delivery of a defibrillation shock therapy based on the received first electrical heart signals; and
   a second implantable device separate from the first implantable device, the second implantable device comprising an implantable bradycardia pacing device configured to receive second electrical heart signals from at least one implantable electrode separate from the at least one subcutaneous electrode, the second implantable device comprising:
   a shock detector circuit configured to detect delivery of shock therapy based on the received second electrical heart signals; and
   a second processor configured to control delivery of a post-shock pacing therapy based on the detected delivery of shock therapy.

2. The system of claim 1, comprising:
   a plurality of subcutaneous electrodes configured to sense the first electrical heart signals; and a plurality of implantable electrodes configured to sense the second electrical signals, the second electrical signals comprising intrinsic electrical heart signals,
wherein the shock detector circuit is configured to detect delivery of shock therapy based on the sensed intrinsic electrical heart signals.

3. The system of claim 1, wherein the second implantable device is configured to be coupled to an intravascular lead, the intravascular lead comprising the at least one implantable electrode, and
wherein the second implantable device does not have shocking capabilities.

4. The system of claim 1, wherein the first implantable device comprises a first energy delivery circuit configured to deliver the defibrillation shock therapy,
wherein the second implantable device comprises a second energy delivery circuit configured to deliver the post-shock pacing therapy, and
wherein the second processor is programmable to disable delivery of post-shock pacing therapy based on programming input indicating that the first energy delivery circuit is unavailable.

5. The system of claim 1, wherein the second processor is configured to control delivery of the post-shock pacing therapy without a communicated request from the first implantable device.

6. The system of claim 1, wherein the second implantable device is configured to receive at least one post-shock pacing therapy parameter, and
wherein the second processor is configured to control the delivery of the post-shock pacing therapy based on the at least one received post-shock pacing therapy parameter.

7. The system of claim 1, wherein the second implantable device is configured to receive at least one post-shock pacing therapy parameter, and
wherein the second processor is configured to enable or disable the delivery of the post-shock pacing therapy based on the at least one received post-shock pacing therapy parameter.

8. The system of claim 1, wherein the second implantable device comprises a ventricular tachyarrhythmia (VT) detector circuit configured to detect a VT based on the received first electrical heart signals, and
wherein the second processor is configured to control delivery of an anti-tachyarrhythmia pacing (ATP) therapy based on the detected VT.

9. The implantable device of claim 8, wherein the second processor is further configured to stop delivery of ATP when a shock therapy is detected by the shock detector circuit.

10. The system of claim 8, wherein the second processor is configured to start delivery of ATP therapy when the VT detector circuit detects a VT based on the received first electrical heart signals and stop delivering ATP therapy when a shock is detected, wherein risk of acceleration initiated by the ATP therapy is mitigated by delivery of defibrillation therapy by the implantable defibrillator device.

11. A method comprising:
receiving first electrical heart signals from at least one subcutaneous electrode using a first implantable device;
controlling delivery of a defibrillation shock therapy based on the received first electrical heart signals using the first processor of the first implantable device;
receiving second electrical heart signals from at least one implantable electrode separate from the at least one subcutaneous electrode using a second implantable device, the second implantable device comprising an implantable bradycardia pacing device;
detecting delivery of shock therapy based on the received second electrical heart signals using a shock detector circuit of the second implantable device;
controlling delivery of a post-shock pacing therapy based on the detected delivery of shock therapy using a second processor of the second implantable device.

12. The method of claim 11, comprising:
sensing the first electrical heart signals using a plurality of subcutaneous electrodes; and
sensing the second electrical signals using a plurality of implantable electrodes, the second electrical signals comprising intrinsic electrical heart signals;
wherein controlling delivery of the post-shock pacing therapy comprises controlling delivery of the post-shock pacing therapy based on the sensed intrinsic electrical heart signals.

13. The method of claim 11, comprising:
delivering the defibrillation shock therapy using a first energy delivery circuit of the first implantable medical device;
delivering the post-shock pacing therapy using a second energy delivery circuit of the second implantable device; and
disabling, using the second processor, delivery of post-shock pacing therapy based on programming input indicating that the first energy delivery circuit is unavailable.

14. The method of claim 11, comprising:
controlling delivery of the post-shock pacing therapy using the second processor without a communicated request from the first implantable device,
wherein the second implantable device does not have shocking capabilities.

15. The method of claim 11, comprising:
detecting a ventricular tachyarrhythmia (VT) based on the received first electrical heart signals using a VT detector circuit of the second implantable device;
controlling delivery of an anti-tachyarrhythmia pacing (ATP) therapy based on the detected VT using the second processor; and
stopping delivery of ATP, using the second processor, when a shock therapy is detected by the shock detector circuit.

16. The method of claim 11, comprising:
detecting a ventricular tachyarrhythmia (VT) based on the received first electrical heart signals using a VT detector circuit of the second implantable device;
controlling delivery of an anti-tachyarrhythmia pacing (ATP) therapy based on the detected VT using the second processor; and
starting delivery of ATP therapy, using the second processor, when the VT detector circuit detects a VT based on the received first electrical heart signals and stop delivering ATP therapy when a shock is detected, wherein risk of acceleration initiated by the ATP therapy is mitigated by delivery of defibrillation therapy by the implantable defibrillator device.

* * * * *